United States Patent [19]

Alpers et al.

[11] Patent Number: 4,784,981

[45] Date of Patent: Nov. 15, 1988

[54] VANADIUM/PHOSPHORUS MIXED OXIDE CATALYST, PROCESS FOR ITS PREPARATON AND ITS USE

[75] Inventors: Heinz-Jürgen Alpers; Karl-Heinz Heller; Günther Lenz, all of Krefeld, Fed. Rep. of Germany

[73] Assignee: Bayer Aktiengesellschaft, Leverkusen, Fed. Rep. of Germany

[21] Appl. No.: 399,633

[22] Filed: Jul. 19, 1982

[30] Foreign Application Priority Data

Jul. 31, 1981 [DE] Fed. Rep. of Germany ....... 3130343

[51] Int. Cl.$^4$ ..................... B01J 27/198; B01J 27/185
[52] U.S. Cl. ..................................... 502/209; 502/213; 502/211
[58] Field of Search ................ 252/435, 437; 502/213, 502/211

[56] References Cited

U.S. PATENT DOCUMENTS

| | | | |
|---|---|---|---|
| 4,016,105 | 4/1977 | Kerr | 252/437 |
| 4,052,417 | 10/1977 | Slinkard | 260/346.75 |
| 4,116,868 | 9/1978 | Mount et al. | 252/437 X |
| 4,171,316 | 10/1979 | Pedersen | 260/346.75 |
| 4,222,945 | 9/1980 | Higgins et al. | 252/437 X |
| 4,225,465 | 9/1980 | Brener | 252/437 X |
| 4,293,498 | 10/1981 | Lemanski et al. | 252/437 X |
| 4,360,453 | 11/1982 | Lemanski et al. | 252/437 X |
| 4,396,535 | 8/1983 | Brener et al. | 252/437 X |

FOREIGN PATENT DOCUMENTS 0031696 7/1981 European Pat. Off. .

*Primary Examiner*—H. M. S. Sneed
*Assistant Examiner*—William G. Wright
*Attorney, Agent, or Firm*—Sprung Horn Kramer & Woods

[57] ABSTRACT

The invention relates to a vanadium/phosphorus mixed oxide catalyst, a process for its preparation and its use for the preparation of maleic anhydride.

The catalyst according to the invention is prepared by reacting a vanadium(V) compound with phosphoric acid and/or a compound forming phosphoric acid with heating, optionally in the presence of water, and subsequently treating the product obtained after the reaction with organic solvents and/or diluents having reducing activity, optionally in the presence of a promoter, at an elevated temperature.

30 Claims, No Drawings

VANADIUM/PHOSPHORUS MIXED OXIDE CATALYST, PROCESS FOR ITS PREPARATON AND ITS USE

The invention relates to a vandadium/phosphorus mixed oxide catalyst, a process for its preparation and its use for the preparation of maleic anhydride.

Vanadium/phosphorus mixed oxide catalysts and their use for the preparation of maleic anhydride from $C_4$ hydrocarbons by gas phase oxidation have been known for a long time.

Thus a vanadium/phosphorus mixed oxide catalyst is already described in the U.S. Pat. No. 2,773,838, with the aid of which a butene/butane mixture is oxidized to maleic anhydride (see Example II). In this, the catalyst is prepared by reaction of aqueous phosphoric acid with ammonium vanadate ($NH_4VO_3$) (see Example I). Yields of maleic anhydride are achieved on oxidation of the butene/butane mixture which are not more than 55.8% by weight, relative to the proportion of butene employed (see Table II).

In order to increase further the yields of maleic anhydride with the aid of the vanadium/phosphorus mixed oxide catalyst, the catalyst or its preparation has been modified in many different ways in the past. For example, it has been attempted to increase the activity and selectivity of the vanadium/phosphorus mixed oxide catalyst by doping with other elements, such as W, Sb, Nb and Mo (German Offenlegungsschrift No. 2,750,327), W, Ni, Cd, Zn, Bi, Li, Cu, U, Zr, Hf, Cr, Fe, Mn, Mo and Co (German Offenlegungsschrift No. 2,822,322), by changing the valency of the vanadium (U.S. Pat. No. 3,156,705; German Offenlegungsschrift No. 2,328,755), by reacting a vanadium-containing material with o-phosphoric acid in an anhydrous organic liquid in the liquid phase (German Auslegeschrift No. 2,700,635 and U.S. Pat. No. 4,244,879), by activation of a precursor of a vanadium/phosphorus mixed oxide catalyst by means of heat treatment under certain conditions (German Offenlegungsschrift No. 2,256,909) or by treatment with an acid which is stronger than phosphoric acid and subsequent extraction to remove soluble components (German Offenlegungsschrift No. 2,822,322).

Vanadium/phosphorus mixed oxide catalysts are obtained in all these modifications of the process, some of which are technically complicated, but they provide only unsatisfactory yields of maleic anhydride on oxidation of $C_4$ hydrocarbons, and this adversely affects the economics of the process for the preparation of maleic anhydride.

The invention relates to a new vanadium/phosphorus mixed oxide catalyst, obtained by reacting a vanadium (V) compound with phosphoric acid and/or a compound forming phosphoric acid with heating, optionally in the presence of water, and subsequent treatment of the product obtained after the reaction with at least one organic solvent and/or diluent having reducing activity, optionally in the presence of a promoter, at an elevated temperature.

The invention also relates to a process for the preparation of a vanadium/phosphorus mixed oxide catalyst, characterised in that a vanadium (V) compound is reacted with phosphoric acid and/or a compound forming phosphoric acid with heating, optionally in the presence of water, and the product obtained after the reaction is subsequently treated with at least one organic solvent and/or diluent having reducing activity, optionally in the presence of a promoter, at an elevated temperature.

In addition, the invention relates to the use of the vanadium/phosphorus mixed oxide catalyst for the preparation of maleic anhydride from $C_4$ hydrocarbons in the vapour phase.

For the preparation of the vanadium/phosphorus mixed oxide catalyst according to the invention, a vanadium (V) compound is initially reacted with phosphoric acid, or a compound forming phosphoric acid, at an elevated temperature, optionally in the presence of water, care being taken that the major part of the vanadium compound employed remains in the 5-valent state. For this reason, no substantial amounts of reducing compounds should be present during the reaction. The vanadium and phosphorus compounds employed should also not contain any reducing anions. The product obtained after the reaction and consisting of phosphates of 5-valent vanadium, the so-called catalyst precursor, has a vanadium/phosphorus atomic ratio of about 1:0.9 to 1.5, prefeably 1:1.0 to 1.3.

The catalyst precursor is generally prepared in such a manner that the vanadium (V) compound and the phosphoric acid or the compound forming phosphoric acid, optionally in the presence of water, are heated, with thorough mixing, to temperatures of about 80° to 180° C., preferably 100° to 150° C., for about 1 to 24 hours, preferably 4 to 8 hours.

According to one mode of preparation, the mixing of the reactants can be carried out in a kneader or another customary mixing apparatus, it being possible to add sufficient water to produce a flowable paste. Normally, about 0 to 30% by weight, preferably 5 to 15% by weight of water, relative to the total mixture, is thereby employed. The crude product obtained by this is isolated by evaporation of the paste-like reaction mixture to dryness at temperatures from about 100° to 200° C.

According to another mode of preparation, the vanadium (V) compounds and the phosphoric acid and/or the compounds forming phosphoric acid are reacted with the addition of about 30 to 90%, preferably 40 to 60%, of water, relative to the total mixture, in an aqueous suspension, the reaction product separating out in crystalline form. The reaction product is then filtered off, advantageously washed with water and then with acetone and then dried at about 100° to 180° C.

Vanadium (V) compounds which can be employed are, for example, vanadium pentoxide, ammonium vanadate and/or sodium vanadate. Vanadium pentoxide is preferably employed.

Compounds forming phosphoric acid which can be employed for the process according to the invention are phosphorus pentoxide, m-phosphoric acid and/or polyphosphoric acids. When using compounds forming phosphoric acid, it can be advantageous to carry out the reaction in the presence of water. In this case, it is advantageous to add sufficient water to convert the compounds forming phosphoric acid almost completely into phosphoric acid.

The amount of phosphoric acids and/or compound forming phosphoric acid employed for the preparation of the catalyst precursor, relative to the amount of vanadium compound employed, depends on the mode of preparation.

If the solid precursor is obtained from the reaction mixture by evaporation to dryness, the atomic ratio of vanadium to phosphorus equals that of the finished precursor, that is 1:0.9 to 1:1.5, preferably 1:1.0 to 1:1.3.

If, on the other hand, the solid catalyst precursor is separated off from the reaction mixture by filtration, an excess of phosphoric acid can be used. In this case, the atomic ratio of vanadium to phosphorus in the mixture employed can be about 1:0.9 to 1:30, preferably 1:3 to 15.

The catalyst precursor obtained is subsequently treated, optionally in a milled form, at an elevated temperature (about 80° to 200° C., preferably 90° to 120° C.), in a suspended form with at least one organic solvent and/or diluent having reducing activity, optionally, in the presence of additional phosphoric acid and optionally in the presence of catalyst promoters, the small amounts of water produced during the treatment being optionally removed from the reaction mixture, for example by distillation. Preferably, only the major amount of water is removed. However it is also possible to carry out the treatment of the catalyst precursor with reducing solvents and/or diluents in the presence of originally added water.

Suitable organic solvents and/or diluents are polar compounds containing carbon, oxygen and hydrogen, which contain 1 to 10, preferably 3 to 6, carbon atoms in the molecule, such as aliphatic, cycloaliphatic or araliphatic, saturated or unsaturated alcohols, aldehydes, ketones acids and esters, particularly alcohols, aldehydes and acids.

Examples of alcohols employed are: propan-1-ol, propan-2-ol, 2-methylpropan-1-ol, butan-1-ol, pentanols, hexanols, cyclohexanol and benzyl alcohol, preferably butan-1-ol, 2-methylpropan-1-ol, of aldehydes: propanal, butanal, 2-methylpropanal, pentanal, hexanal and benzaldehyde, preferably butanal, 2-methylpropanal and pentanal, of ketones: acetone, butanone, pentanone and cyclohexanone, preferably pentanone, of acids: formic acid, acetic acid, propionic acid, oxalic acid, citric acid and ascorbic acid, preferably acetic acid and oxalic acid, and of esters: ethyl acetate, propyl acetate, butyl acetate, ethyl propionate and butyl propionate, preferably butyl acetate.

The organic solvent and/or diluent can be employed either alone or as mixtures with one another. When the organic solvent and/or diluent itself has no reducin property, it should only be employed as a mixture with another organic solvent and/or diluent having reducing activity.

In general the organic solvents and/or diluents are employed in amounts of about 0.5 to 20, preferably 2 to 10, parts by weight relative to 1 part of the catalyst precursor.

The amount of phosphoric acid optionally employed in the treatment of the catalyst precursor with the organic solvents and/or diluents, the phosphoric acid normally being employed in a form which is about 85 to 100% by weight, preferably 100% by weight, is about 0.01 to 0.5, preferably 0.1 to 0.2, parts, relative to 1 part of the precursor.

Examples of suitable catalyst promoters are elements of the 1st, 2nd, 7th and/or 8th sub-groups of the periodic system of the elements (Mendeleev). The following are mentioned by way of example: copper, silver, zinc, cadmium, manganese, iron, cobalt, nickel, palladium and/or platinum, preferably iron and/or manganese.

The catalyst promoters can be employed in elemental form or in the form of their compounds, such as the carbonates, hydrogen carbonates, phosphates, acetates and/or oxalates, preferably the phosphates and/or the oxalates.

The amount of promoter to be employed is advantageously such that the atomic ratio of promoter to vanadium is about 0.01 to 0.1, preferably 0.02 to 0.07.

Of course, it is also possible to add the catalyst promoters to the finished vanadium/phosphorus mixed oxide catalyst, instead of during the treatment of the catalyst precursor, during its preparation or after the treatment of the precursor with organic solvents and/or diluents.

One possible method of treating the catalyst precursor with an organic solvent and/or diluent consists of heating the precursor, which may optionally be milled, with phosphoric acid and the organic solvent and/or diluent, optionally with the addition of a promoter, at temperatures of about 80° to 200° C., preferably 90° to 120° C., with thorough mixing, the small amounts of water formed during the treatment being removed from the reaction mixture in a customary manner, optionally using water-immiscible aliphatic and/or aromatic hydrocarbons, such as pentane, cyclohexane, toluene and/or xylene (azeotropic distillation). To improve the separation of water, a distillation column with 1 to 10 theoretical plates can also be used.

After about 5 to 500, preferably 10 to 50 hours of treatment of the catalyst precursor, which is now in a lower valency state (mean valency of the vanadium is about 3.9 to 4.2), the suspenion can either be evaporated to dryness at temperatures of about 80° to 150° C., or the solid material can be separated out of the suspension by filtration. The recovered organic solvent and/or diluent can thereby be reused for other batches.

The solid material which has been filtered off is advantageously dried at about 100° to 150° C. in the presence of air or nitrogen or in vacuo.

The vanadium/phosphorus mixed oxide catalyst obtained can then be actived by heat treatment at temperatures up to about 600° C., preferably at 350° to 450° C. in a customary manner and then be converted into a suitable form for industrial application for example by compression to shaped catalyst particles or spreading in perforated plates, optionally with the addition of inert diluting agents, such as silica, alumina and/or titania. Of course, it is also possible to apply the catalyst mass to the customary inert supports, such as alumina, silicon carbide or steatite by known methods.

The vanadium/phosphorus mixed oxide catalyst can be used in a known manner for the oxidation of straight-chain $C_4$ hydrocarbons, such as but-1-ene, cis- and trans-but-2-ene, and/or n-butane or a mixture thereof, preferably butene and butene/butane mixtures, with air to maleic anhydride (see in this connection, for example, Ullmann, Enzyklopädie der Technischen Chemie [Encyclopedia of Industrial Chemistry], Volume 9, page 147 et seq. Volume 16, page 408 et seq.).

This oxidation to maleic anhydride by the use of air is e.g. carried out in that a mixture of air and the mentioned $C_4$ hydrocarbons is passed at an elevated temperature over the catalyst arranged in a fixed bed. The concentration of the $C_4$ hydrocarbon can be of from 25 to 90 g per normal $m^3$ of air, preferably 35–60 g.

The catalyst is usually arranged in vertical tubes which are cooled externally by a salt melt. By adjusting the temperature of this salt melt the catalyst temperature is adjusted to about 330°–550° C., preferably 380°–500° C.

Usually the feed gas mixture passes the catalyst tube from the top to the bottom. However, the adverse direction is also possible. The amount of feed gas mixture referred to the catalyst volume is defined by a space velocity of 500–5000 $h^{-1}$, preferably 1000–4000 $h^{-1}$.

As is shown by the comparison experiments which are listed in the examples of the presenct application, and which were carried out under industrial conditions with known vanadium/phosphorus mixed oxide catalysts, which were prepared, inter alia, in accordance with German Auslegeschrift No. 2,700,635 and German Offenlegungsschrift No. 2,822,322, and were converted into a form suitable for industrial application, the vanadium/phosphorus mixed oxide catalyst prepared according to the invention brings about an improved selectivity, combined with a considerable increase in yield of maleic anhydride of more than 10% by weight, relative to the $C_4$ hydrocarbon initially employed.

The following examples are intended to illustrate the preparation of the catalyst according to the invention and the use of the catalyst according to the invention for the preparation of maleic anhydride.

EXAMPLE 1

(a) Preparation of the catalyst precursor;
Charge:
1 kg of vanadium pentoxide $V_2O_5$
9 kg of 85% strength phosphoric acid ($H_3PO_4$)
8 kg of water Water and phosphoric acid were heated to boiling and the vanadium pentoxide was then introduced with stirring. After 8 hours of stirring and boiling under reflux, the mixture was cooled down to 20° C., the solid was filtered off, washed with water, and then washed thoroughly with acetone in order to remove adhering excess phosphoric acid. The product was then dried at 150° C.

(b) After-treatment of the catalyst precursor with isobutanol/n-butanal;
Charge:
1 kg of catalyst precursor (dry)
121 g of phosphoric acid (100% strength)
3.7 kg of isobutanol
480 g of butanal The components were boiled together under reflux, with stirring. The vapours being formed were directed over a distillation column and a condenser to a water separator. The length of the distillation column uses should correspond to 1 to 2 theoretical stages. During the period of boiling, which totalled 50 hours, 50 to 100 ml of water were obtained in the water separator and separated off. After the end of the period of boiling, the mixture was cooled down to about 20° C. and the solid filtered off. The crude product obtained was dried at 100° C. under nitrogen.

(c) Further processing of the treated catalyst precursor to give catalyst beads

The dried product obtained under (b) was heated from about 20° C. to 410° C. at a heating rate of 150° C./h, and maintained at this temperature for 5 hours. The product heat-treated in this way was milled and compressed, with the addition of about 6% of aluminium stearate, to beads with a diameter of 6.6 mm.

The catalyst has an atomic ratio of vanadium to phosphorus of 1:1.2.

EXAMPLE 2

The procedure corresponded to Example 1, but on after-treatment 55.5 g of iron oxalate ($FeC_2O_4 \times 2H_2O$) were added to the batch. The vanadium/iron atomic ratio corresponds to 1:0.05.

EXAMPLE 3

The crude product was prepared as described under Example 1, but on after-treatment 222 g of iron oxalate were added to the batch (atomic ratio of vanadium to iron as 1:0.2).

EXAMPLE 4

(a) Preparation of the catalyst precursor;
Charge:
736 g of $V_2O_5$
1,118 g of $H_3PO_4$ (85% strength)
76 g of iron oxalate The starting materials were mixed in a kneader for 3 hours without using other solvents, heated to 120° C. and maintained at this temperature for 2 hours.

(b) After-treatment of the catalyst precursor with isobutanol/n-butanal;
Charge:
1,450 g of precursor from stage (a)
3.7 kg of isobutanol
480 g of n-butanal Further treatment was carried out as described under Example 1 (atomic ratio of vanadium to iron as 1:0.05 and vanadium to phosphorus as 1:1.2).

EXAMPLE 5

The procedure corresponded to Example 1, but, on after-treatment, 35.5 g of $MnCO_3$ were added to the batch (atomic ratio of vanadium to manganese as 1:0.05).

EXAMPLE 6

The procedure corresponded to Example 1, but, on after-treatment, 55.5 g of iron oxalate ($FeC_4O_4 \times 2H_2O$) were added to the batch and the after-treatment was carried out with a mixture of 3.7 kg of n-butanol and 480 g of butanal.

EXAMPLE 7

The procedure corresponded to Example 6, with the change that the after-treatment was carried out with a mixture of 3.7 kg of isobutanol and 700 g of benzyl alcohol.

EXAMPLE 8

The procedure corresponded to Example 6, with the change that the after-treatment was carried out with 4.2 kg of isobutanol and was extended to 300 hours.

EXAMPLE 9

The procedure corresponded to Example 6, with the change that the after-treatment was carried out with a mixture of 3.7 kg of glacial acetic acid and 600 g of butanal, and that no water separator was used during the after-treatment.

EXAMPLE 10

(Comparison example, omitting after-treatment of the catalyst precursor according to the invention)
Charge:

1,100 g of catalyst precursor with 10% residual water, prepared according to Example 1 (a), but without complete drying.
117 g of 85% strength H$_3$PO$_4$
2.5 l of water
48 g of FePO$_4$ The components were mixed and boiled with stirring under reflux for 4 hours. The mixture was then cooled down to 20° C., and the solid was filtered off under suction and dried at 150° C. The subsequent treatment was carried out as described under Example 1 (c) (atomic ratio V:P:Fe as 1:1.2:0.5).

EXAMPLE 11

(Comparison example in accordance with German Auslegeschrift No. 2,700,635)
Charge:
693 g of V$_2$O$_5$—(Component 1)
2,700 ml of isobutanol—(Component 2)
900 ml of benzyl alcohol—(Component 3)
900 g of phoshoric acid—(Component 4)
900 ml of isobutanol—(Component 5)
Apparatus:
6 l flask with stirrer, dropping funnel for additions and condenser with water separator.
Procedure:
Components 1, 2, and 3 were initially introduced into the apparatus and stirred for 5 hours under reflux. The mixture was then cooled down to 60° C. and the solution of Component 4 in Component 5 was added slowly. The mixture was stirred a further 20 hours under reflux. After cooling down to room temperature, the solid material was filtered off and dried. Further processing was carried out as described under Example 1 (c) (atomic ratio V:P as 1:1.2).

EXAMPLE 12

(Comparison example in accordance with German Auslegeschrift No. 2,700,635)
Charge:
772.5 g of V$_2$O$_5$—(Component 1)
64.05 g of FePO$_4$—(Component 2)
2,000 ml of isoubtanol—(Component 3)
1,000 ml of benzyl alcohol—(Component 4)
958 g phosphoric acid—(Component 5)
2,000 ml of isobutanol—(Component 6)
Apparatus as described under Example 7.
Procedure:
Components 1, 2, 3 and 4 were boiled with stirring and under reflux for 22 hours. The mixture was then cooled down to room temperature and the solution of Component 5 in Component 6 was slowly added. The mixture was then boiled under reflux for a further 20 hours. After cooling down to 20° C., the solid was filtered off, dried and further processed as in Example 1(c) (atomic ratio V:P:Fe as 1:1.2:0.05).

EXAMPLE 13

(Comparison example in accordance with German Auslegeschrift No. 2,700,635)
Charge:
772.5 g V$_2$O$_5$—(Component 1)
256.2 g of FePO$_4$—(Component 2)
2,000 ml of isobutanol—(Component 3)
1,000 ml of benzyl alcohol—(Component 4)
833 g of phosphoric acid—(Component 5)
2,000 ml of isobutanol—(Component 6)
Procedure as described under Example 12 (atomic ratio V:P:Fe as 1:1.2:0.2).

EXAMPLE 14

(Comparison example in accordance with German Offenlegungsschrift No. 2,822,322)
(a) 606 g of vanadium pentoxide were boiled with 7,900 ml of concentrated hydrochloric acid under reflux for 2 hours.

891 g of 88% strength phosphoric acid was added to the dark blue solution obtained and, after boiling for 2 hours under reflux, the solution was concentrated to 2,000 ml residual volume.

The residue was boiled with 2,000 ml of concentrated hydrochloric acid under reflux for 1 hour, then evaporated and the solid material obtained was dried at 110° C.

(b) The dried product was boiled with water (20 ml/g) for 1 hour and filtered hot. The filtration residue was washed with a little water and dried at 150° C.

Further processing was carried out as described under Example 1 (c) (atomic ratio V:P as 1:1.2).

EXAMPLE 15

(Comparison example in accordance with German Offenlegungsschrift No. 2,822,322)

A solid material which had been prepared in analogy to Example 10 was boiled with isobutanol (20 ml/g) for 1 hour, filtered hot, washed with a little isobutanol and dried at 150° C. Further processing was carried out as described under Example 1 (c) (atomic ratio V:P as 1:1.2).

Use of the vanadium/phosphorus mixed oxide catalysts

The experiments are intended to provide data on the behaviour during the industrial preparation of maleic anhydride. For this reason, single tube reactors were used, which correspond to industrial reactors in their dimensions and behaviour.
Dimensions of the reaction tubes:
Diameter 25 mm
Length 3,500 mm
Catalyst packing 2,500 mm The catalyst was inside the tubes, and the tubes were surrounded by a fused salt, the temperature of which could be varied. In each case, 1 l of the catalyst to be tested was used. The material introduced was a mixture of C$_4$ hydrocarbons of the following (typical) composition:
19.7% n-butane
4.5% i-butane
42.3% n-but-1-ene
13.7% cis-but-2-ene
19.3% trans-but-2-ene A reaction gas with 1.5% by volume of hydrocarbon was prepared from the mixture of hydrocarbons employed and air and 2.7 m$_n^3$/h of this gas were passed through the catalyst packing (space velocity=2700 h$^{-1}$). The space velocity is to be understood as the gas volume under normal conditions passed through per catalyst volume. The maleic anhydride produced (then in the hydrolysed form as maleic acid) was collected by washing the exit gas with water and its amount was determined by potentiometric titration. The optimum temperature of the salt bath, that is the temperature at which the maximum yield of MA was obtained, was found by varying the temperature of the fused salt. The values for the yields reported in the following table indicate the maleic anhydride (MA) yield in percent by weight, relative to butene employed.

Compilation of the MA yields obtained

| Example | Vanadium/phosphorus mixed oxide catalyst Atomic ratios V:P:Additive | Bath temperature for the reaction to MA (°C.) | Yield of MA (% by weight) |
|---|---|---|---|
| 1 | 1 1.2 — | 450 | 94 |
| 2 | 1 1.2 0.05 Fe | 430 | 103 |
| 3 | 1 1.2 0.20 Fe | 460 | 78 |
| 4 | 1 1.2 0.05 Fe | 450 | 100 |
| 5 | 1 1.2 0.05 Mn | 450 | 100 |
| 6 | 1 1.2 0.05 Fe | 400 | 86 |
| 7 | 1 1.2 0.05 Fe | 420 | 97 |
| 8 | 1 1.2 0.05 Fe | 420 | 100 |
| 9 | 1 1.2 0.05 Fe | 410 | 97 |
| Comparison Examples | | | |
| 10 | 1 1.2 0.05 Fe | 450 | 55 |
| 11* | 1 1.2 | 450 | 82 |
| 12* | 1 1.2 0.05 Fe | 430 | 83 |
| 13* | 1 1.2 0.20 Fe | 460 | 64 |
| 14** | 1 1.2 | 450 | 76 |
| 15** | 1 1.2 | 450 | 80 |

*No. 11, 12, 13 in accordance with German Auslegeschrift 2,700,635
**No. 14, 15 in accordance with German Offenlegungsschrift 2,822,322

Legend to the compilation:
Comparison Example No. 10—(omitting after-treatment)
Comparison Example No. 11—(compare Example 1)
Comparison Example No. 12—(compare Examples 2, 4, 6–9)
Comparison Example No. 13—(compare Example 3)
Comparison Example No. 14—(compare Example 1)
Comparison Example No. 15—(compare Example 1)

EXAMPLE 16

The catalyst prepared according to Example 4 was tested by the procedure described above, the inlet concentration of the hydrocarbon being, however, 1.95% by volume. The yield of MA as defined above was 101% at an optimum bath temperature of 410° C.

What is claimed is:

1. A process for the preparation of vanadium phosphorus mixed oxide-containing catalysts comprising
    (a) introducing a pentavalent vanadium compound and a pentavalent phosphorus compound into an aqueous medium wherein the aqueous medium is free from agents which would substantially reduce the pentavalent vanadium compound;
    (b) forming a substantially pentavalent catalyst precursor in the aqueous medium;
    (c) recovering the pentavalent catalyst precursor from the aqueous medium;
    (d) introducing the pentavalent catalyst precursor into a substantially organic liquid medium capable of reducing at least a portion of the vanadium to a valence state of about +4;
    (e) effecting reduction of the vanadium;
    (f) recovering the resulting partially reduced catalyst precursor from the organic liquid medium;
    (g) calcining the partially reduced catalyst precursor, which further comprises introducing a promoter element-containing compound into the aqueous medium, or into the organic liquid medium prior or subsequent to the reduction of the vanadium.

2. A process as in claim 1 wherein said organic liquid is selected from alcohols, ketones and mixtures thereof.

3. A process as in claim 2 wherein said organic liquid is selected from isopropanol and isobutanol.

4. A process as in claim 2 wherein said organic liquid comprises an alcohol.

5. A process as in claim 4 wherein said alcohol comprises isobutanol.

6. A process as in claim 1 wherein reduction is effected by heating.

7. A process as in claim 1 wherein said promoter element is selected from Mn, Co, Fe, Zn, Ni, Cu, Cd or mixtures thereof.

8. A process as in claim 1 wherein said promoter element is selected from the group consisting of platinum and palladium.

9. A process according to claim 1, wherein said organic liquid medium capable of reducing at least a portion of the vanadium to a valence state of about +4 is an aldehyde.

10. A process according to claim 1, wherein said organic liquid medium capable of reducing at least a portion of the vanadium to a valence state of about +4 is sec-butanol.

11. A process according to claim 1, wherein said organic liquid medium capable of reducing at least a portion of the vanadium to a valence state of about +4 is an unsaturated alcohol.

12. A process according to claim 1, wherein said pentavalent phosphorus compound is selected from the group consisting of pentoxide, polyphosphoric acid and pyrophosphoric acid.

13. A process according to claim 1, wherein the resultant partially reduced catalyst is disposed on a catalyst support selected from the group consisting of alumina, silica, titania and silicon carbide.

14. A process according to claim 1, wherein drying in step (g) occurs by evaporation and the vanadium/phosphorus atomic ratio is 1:0.9 to 1.5.

15. A process according to claim 1, wherein in step (a) the vanadium compound and the pentavalent phosphorus compound are heated to 80° to 180° C. for 1 to 24 hours.

16. A process according to claim 1, wherein in step (f) the precursor is recovered by filtration and the vanadium/phosphorus atomic ratio is 1:0.9 to 1:30.

17. A process according to claim 1, wherein the organic liquid is employed in an amount of 0.5 to 20 parts by weight, relative to the catalyst precursor.

18. A process according to claim 1, wherein the atomic ratio of the promoter to the vanadium is 0.01 to 0.1.

19. An oxidation catalyst comprising mixed oxides of vanadium and phosphorus prepared by
    (a) introducing a pentavalent vanadium compound and a pentavalent phosphorus compound into an aqueous medium wherein the aqueous medium is free from agents which would substantially reduce the pentavalent vanadium compound;
    (b) forming a substantially pentavalent catalyst precursor in the aqueous medium;
    (c) recovering the pentavalent catalyst precursor from the aqueous medium;
    (d) introducing the pentavalent catalyst precursor into a substantially organic liquid medium capable of reducing at least a portion of the vanadium to a valence state of about +4, the catalyst additionally containing a promoter element selected from the group consisting of Mn, Co, Fe, Zn, Ni, Cu, Cd or mixtures thereof.

20. An oxidation catalyst as in claim 19 additionally containing a promoter element selected from the group consisting of platinum and palladium.

21. An oxidation catalyst according to claim 19, wherein said organic liquid medium capable of reducing at least a portion of the vanadium to a valence state of about +4 is an aldehyde.

22. An oxidation catalyst according to claim 19, wherein said organic liquid medium capable of reducing at least a portion of the vanadium to a valence state of about +4 is sec-butanol.

23. An oxidation catalyst according to claim 19, wherein said organic liquid medium capable of reducing at least a portion of the vanadium to a valence state of about +4 is an unsaturated alcohol.

24. An oxidation catalyst according to claim 19, wherein said pentavalent phosphorus compound is selected from the group consisting of phosphorus pentoxide, polyphosphoirc acid and pyrophosphoric acid.

25. An oxidation catalyst according to claim 19, wherein the resultant partially reduced catalyst is disposed on a catalyst support selected from the group consisting of alumina, silica, titania and silicon carbide.

26. An oxidation catalyst according to claim 19, wherein drying step (g) occurs by evaporation and the vanadium/phosphorus atomic ratio is 1:0.9 to 1.5.

27. An oxidation catalyst according to claim 19, wherein in step (a) the vanadium compound and the pentavalent phosphorus compound are heated to 80° to 180° C. for 1 to 24 hours.

28. An oxidation catalyst according to claim 19, wherein in step (f) the precursor is recovered by filtration and the vanadium/phosphorus atomic ratio is 1:0.9 to 1:30.

29. An oxidation catalyst according to claim 19, wherein the organic liquid is employed in an amount of 0.5 to 20 parts by weight, relative to the catalyst precursor.

30. An oxidation catalyst according to claim 19, wherein the atomic ratio of the promoter to the vanadium is 0.01 to 0.1.

* * * * *